(12) United States Patent
Gabrielii et al.

(10) Patent No.: US 8,575,418 B2
(45) Date of Patent: Nov. 5, 2013

(54) ABSORBENT ARTICLE WITH VENTILATED TOPSHEET

(75) Inventors: Inge Gabrielii, Västra Frölunda (SE); Anna Nihlstrand, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 304 days.

(21) Appl. No.: 12/747,207

(22) PCT Filed: Dec. 21, 2007

(86) PCT No.: PCT/SE2007/051073
§ 371 (c)(1),
(2), (4) Date: Jun. 10, 2010

(87) PCT Pub. No.: WO2009/082309
PCT Pub. Date: Jul. 2, 2009

(65) Prior Publication Data
US 2010/0274208 A1    Oct. 28, 2010

(51) Int. Cl.
*A61F 13/15* (2006.01)
(52) U.S. Cl.
USPC ............ 604/378; 604/379; 604/380; 604/383; 604/385.01
(58) Field of Classification Search
USPC ............... 604/378, 379, 380, 383, 385.01
See application file for complete search history.

(56) References Cited

U.S. PATENT DOCUMENTS

| 4,451,934 A | 6/1984 | Gioello |
| 6,454,749 B1 | 9/2002 | Lau et al. |
| 2002/0120249 A1 | 8/2002 | Wads et al. |
| 2003/0224146 A1* | 12/2003 | Raidel et al. .................. 428/182 |
| 2006/0058763 A1 | 3/2006 | Cohen et al. |

FOREIGN PATENT DOCUMENTS

| EP | 0 958 802 | 11/1999 |
| EP | 1 609 448 | 12/2005 |
| EP | 1 227 776 | 1/2007 |
| FR | 2 699 813 | 7/1994 |
| GB | 2 284 831 | 6/1995 |
| JP | 4-129553 | 4/1992 |
| WO | WO-91/11161 | 8/1991 |
| WO | 96/16682 | 6/1996 |
| WO | 98/24389 | 6/1998 |
| WO | 03/053300 | 7/2003 |
| WO | 2005/007962 | 1/2005 |

* cited by examiner

*Primary Examiner* — Jacqueline F. Stephens
(74) *Attorney, Agent, or Firm* — Drinker Biddle & Reath LLP (57) ABSTRACT

An absorbent article, such as a diaper, sanitary napkin, incontinence guard or panty liner, including a fluid-permeable nonwoven topsheet located on the wearer-facing side thereof. The nonwoven topsheet includes a plurality of channels arranged side-by-side. The channels are located within the nonwoven topsheet, whereby gas is allowed to pass into, out of and along the channels, thus providing ventilation of the absorbent article.

22 Claims, 5 Drawing Sheets

ABSORBENT ARTICLE WITH VENTILATED TOPSHEET

CROSS-REFERENCE TO PRIOR APPLICATION

This application is a §371 National Stage Application of PCT International Application No. PCT/SE2007/051073 filed Dec. 21, 2007.

FIELD OF THE INVENTION

The present disclosure relates to an absorbent article including a nonwoven topsheet, said topsheet having a structure which provides ventilation of the article.

BACKGROUND

Topsheet materials in absorbent articles like sanitary napkins, diapers, pant diapers, incontinence guards etc. are designed to distribute and move body fluids rapidly through them and into an underlying absorbent structure for storage. Nonwoven fabrics used as topsheet often need to be modified, for example apertured, corrugated and/or treated with fluid modifying agents, such as surfactants or softeners in order to maximize fluid handling and comfort properties.

The combination of moisture and warmth with an absorbent article often creates a microclimate within the article which can be experienced as uncomfortable to the wearer. In addition, this microclimate can also give rise to skin irritations and rashes. Attempts have therefore been made to ventilate absorbent articles, particularly between the topsheet of the article and the wearer's skin.

WO03/053300 describes an absorbent article including an air exchanges means having at least one air exchange duct. Air can thus be discharged into the article in a region between a wearer's skin and the product, via, for example, an external pump.

U.S. Pat. No. 6,454,749 describes a personal care product having a bellows, such that air is forced into the product to the region between the skin and the product. The distribution means (tubing) which directs the air into the product may collapse when air is not flowing.

However there still exists a need for improvement of topsheets for absorbent articles. In particular, it is desirable to encourage air flow and ventilation, to avoid the problems associated with warmth and humidity which often arise in absorbent articles. In addition, it is desirable to promote air flow and ventilation both between the article and the wearer's skin and internally within one or more components of the article.

EP 0 958 802 and US 2002/0120249 describe absorbent articles with structured topsheets.

WO2005/007962 discloses a nonwoven spacer fabric including two separate but interconnected layers, each of which is provided with discrete interconnections so as to provide discrete voids between the two layers of fabric. Use of the fabric in absorbent articles is described, and in Example 1, the voids in the spacer fabric are filled with superabsorbent powder and the resulting material is used as a diaper core.

SUMMARY

In a first aspect, the present disclosure relates to an absorbent article, such as a diaper, sanitary napkin, incontinence guard or panty liner. The article includes a fluid-permeable nonwoven topsheet located on the wearer-facing side thereof. The nonwoven topsheet includes a plurality of channels arranged side-by-side.

The channels are located within the nonwoven topsheet, and at least one end of at least one channel extends to an edge of the article whereby gas is allowed to pass into, out of and along the channels, thus providing ventilation of the absorbent article.

The article may have longitudinal (L) and transverse (T) extensions, wherein channels are arranged side-by-side in the transverse direction (T) of the article and have their main extension in the longitudinal direction (L) of the article. The extension of the channels in the longitudinal direction (L) may be at least 30%, preferably at least 50%, more preferably at least 70% of the extension of the article in the longitudinal direction (L).

Alternatively channels may be arranged side-by-side in the longitudinal direction (L) of the article and have their main extension in the transverse direction (T) of the article. The extension of the channels in the transverse direction (T) is thus at least 30%, preferably at least 50%, more preferably at least 70% of the extension of the article in the transverse direction (T).

In one embodiment, the topsheet may include at least two separate but interconnected layers, each of the layers being provided with discrete interconnections so as to provide a plurality of discrete channels between the two layers.

The channels can be substantially free of solid or liquid material; alternatively some of the channels may contain moisture-capturing and/or liquid-absorbent material, phase change material and/or skin-care agent. The channels may also include porous or resilient fibrous material.

In one particular embodiment, the channels are not sealed in at least one end thereof. Furthermore, at least one longitudinal end of the channels may extend to an edge of the article, particularly the transverse edge. All channels of the absorbent article may extend to an edge of the article, particularly the transverse edge. The channels may include hollow filaments.

The compression recovery of the topsheet is suitably at least 50%, preferably at least 70%, more preferably at least 80%, most preferably 100% in the thickness direction.

DEFINITIONS

The term "absorbent article" refers to a product that is placed against the skin of the wearer to absorb and contain body exudates, like urine, perspiration, faeces and menstrual fluid. Embodiments of the invention mainly refer to disposable absorbent articles, which means articles that are not intended to be laundered or otherwise restored or reused as an absorbent article after use. Examples of disposable absorbent articles include feminine hygiene products such as sanitary napkins, panty liners, tampons and sanitary panties; diapers and pant diapers for infants and incontinent adults; incontinence pads; diaper inserts and the like.

The term "ventilation" is used to describe the movement of air, vapor or moist air in, within, or out of an absorbent article. Ventilation may be active (in that movement of air is promoted or restricted by bodily movements or arrangements such as valves or pumps) or passive (in that movement of air is not promoted or restricted, and is free to move in any direction in the article). Ventilation differs from simple breathability of an article, in that ventilation involves the movement of air or vapor in bulk. Convection is one form of ventilation in which movement of air or vapor is promoted by temperature differences between different regions of an absorbent article (for example the inside and the outside), which can be spontaneous.

In the following, the word "gas" is used to describe air, vapor and moist air. "Vapor" generally refers to water vapor.

A "nonwoven" material is one which is typically manufactured by laying fibers in the form of a sheet or web, and then binding them together in some way such that the integrity of the nonwoven material is maintained. Binding of the fibers can occur mechanically (entangling), thermally or with an adhesive.

A "channel" in the topsheet is defined as an elongate region within the topsheet which is free from topsheet material, while being surrounded by topsheet material along its length. Channels may be straight or curved. In particular embodiments the channels are straight.

BRIEF DESCRIPTION OF THE DRAWINGS

Embodiments of the present invention will now be described with reference to the enclosed Figures, in which.

DETAILED DESCRIPTION OF PREFERRED EMBODIMENTS

Figure 1:
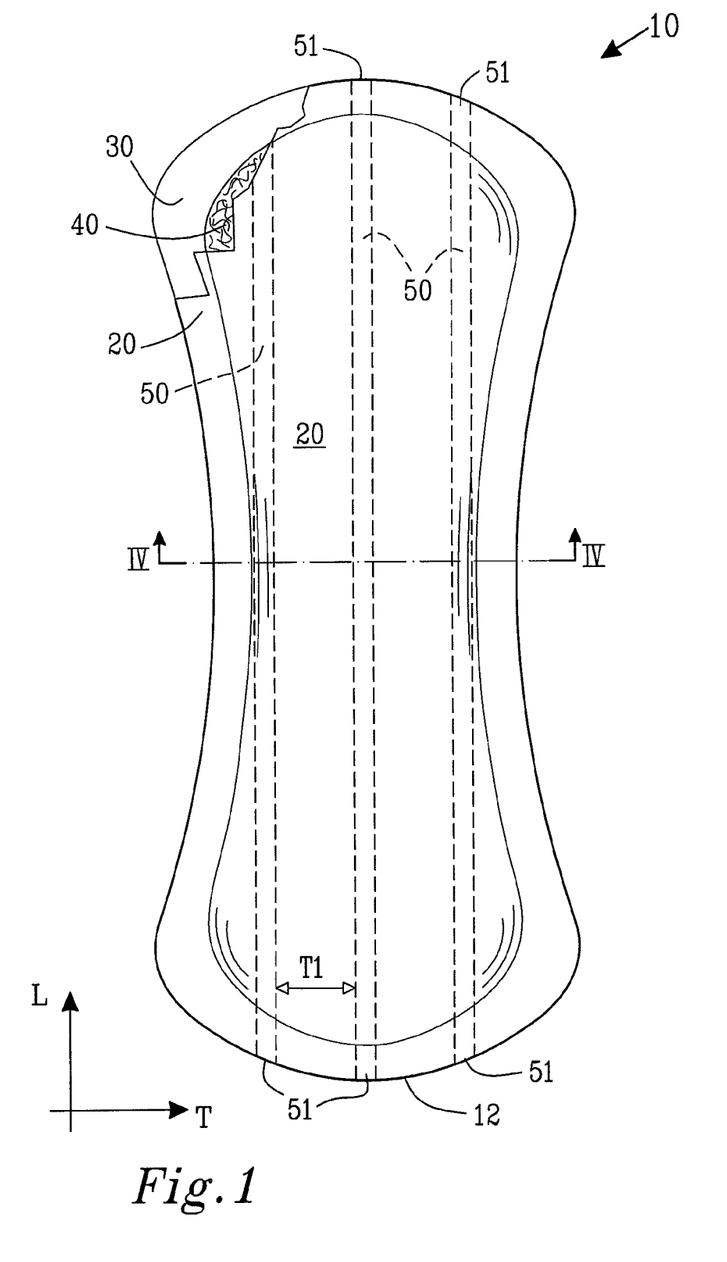
FIG. 1 illustrates an absorbent article according to an embodiment of the invention.

FIG. 1 illustrates an absorbent article 10 according to an embodiment of the invention, in this case a sanitary napkin used by women for absorbing menstrual blood, seen from the wearer-facing side.

The absorbent article 10 illustrated in FIG. 1 has a fluid-permeable nonwoven topsheet 20 located on the wearer-facing side thereof. The nonwoven topsheet 20 thus makes contact with the skin of the wearer, and is typically the first component of the absorbent article which contacts the bodily exudate. The article 10 also includes an absorbent core 40 and a liquid-impermeable backsheet 30. The article 10 also has longitudinal (L) and transverse (T) extensions as illustrated, the longitudinal (L) extension being along the longitudinal (longest) axis of symmetry, and the transverse extension being perpendicular to the longitudinal axis.

The topsheet 20 and the backsheet 30 have a somewhat greater extension in the L-T plane of the article 10 than the absorbent core 40 and extend outside the edges thereof. The topsheet 20 and backsheet 30 are connected to each other within the projecting portions thereof, for example by gluing or welding by heat or ultrasound. The topsheet 20 and/or the backsheet 30 may further be attached to the absorbent core 40 by any method known in the art, such as adhesive, heat bonding etc. The absorbent core 40 may also be unattached to the topsheet 20 and/or the backsheet 30, or only attached in certain regions.

The nonwoven topsheet 20 is fluid-permeable, in that both liquids and gases can pass through it. It may include apertures through which fluid can permeate, or alternatively, fluid may permeate through the spaces between individual fibers 21 in the nonwoven material. To avoid the channels 50 filling up with liquid and blocking the ventilation effect, the channels are preferably liquid-impermeable, or positioned in areas where liquid does not reach. Liquid permeability can be measured using EDANA method WSP70.3 (2005). Using this method, the nonwoven topsheet 20 can have a permeability, or "strike-through time", of less than 10 s, preferably less than 5 s and more preferably less than 2 s.

The nonwoven topsheet 20 may include many different types of fibers 21. For example, natural fibers such as pulp fibers, cotton, jute, wool and hair fibers may be used. Man-made fibers, such as, for example, polyester, viscose, nylon, polypropylene, and polyethylene may also be used, polypropylene and polyester being preferred. Mixtures of different fibers types may also be used, for example a 50/50 mix of polyester and viscose. Bicomponent fibers or binder fibers may also be used. Suitably, the nonwoven topsheet includes a majority (i.e. over 50 weight %) of man-made fibers. Nonwoven materials including man-made fibers are less likely to retain liquid and thus have a dry surface feel.

The topsheet 20 may be treated with a chemical agent to improve one or more of its properties. For example, treatment of the topsheet with surfactants will make it more liquid-permeable. Treatment of the topsheet 20 with a lotion, such, for example as described in EP1227776 provides a softer, more comfortable feel to the wearer, and improved skin properties.

The length of the fibers 21 included in the nonwoven topsheet 20 can be 1-100 mm, and preferably 10-60 mm. Continuous fibers may even be used. The fibers 21 have a linear mass density which lies between 0.05 dtex and 25 dtex, preferably between 0.1 and 10 dtex, more preferably between 0.5 and 3 dtex. If the topsheet 20 contains continuous or staple fibers 21 over approximately 5 dtex which need to be hydroentangled, they are advantageously combined with staple fibers of a lower linear mass density.

The basis weight of the nonwoven topsheet 20 is significant. A basis weight which is too high will result in a stiff, inflexible topsheet which is uncomfortable to the wearer. A basis weight which is too low may result in a weak topsheet, which may not prevent the contents of the article 10 (for example superabsorbent material) from escaping. Suitably, the basis weight of the nonwoven topsheet 20 is at least 10 grams per square meter (gsm), preferably at least 20 gsm, more preferably at least 40 gsm. Furthermore, the basis weight of the nonwoven topsheet 20 is suitably no more than 400 gsm, preferably no more than 250 gsm, more preferably no more than 100 gsm.

Figure 2:
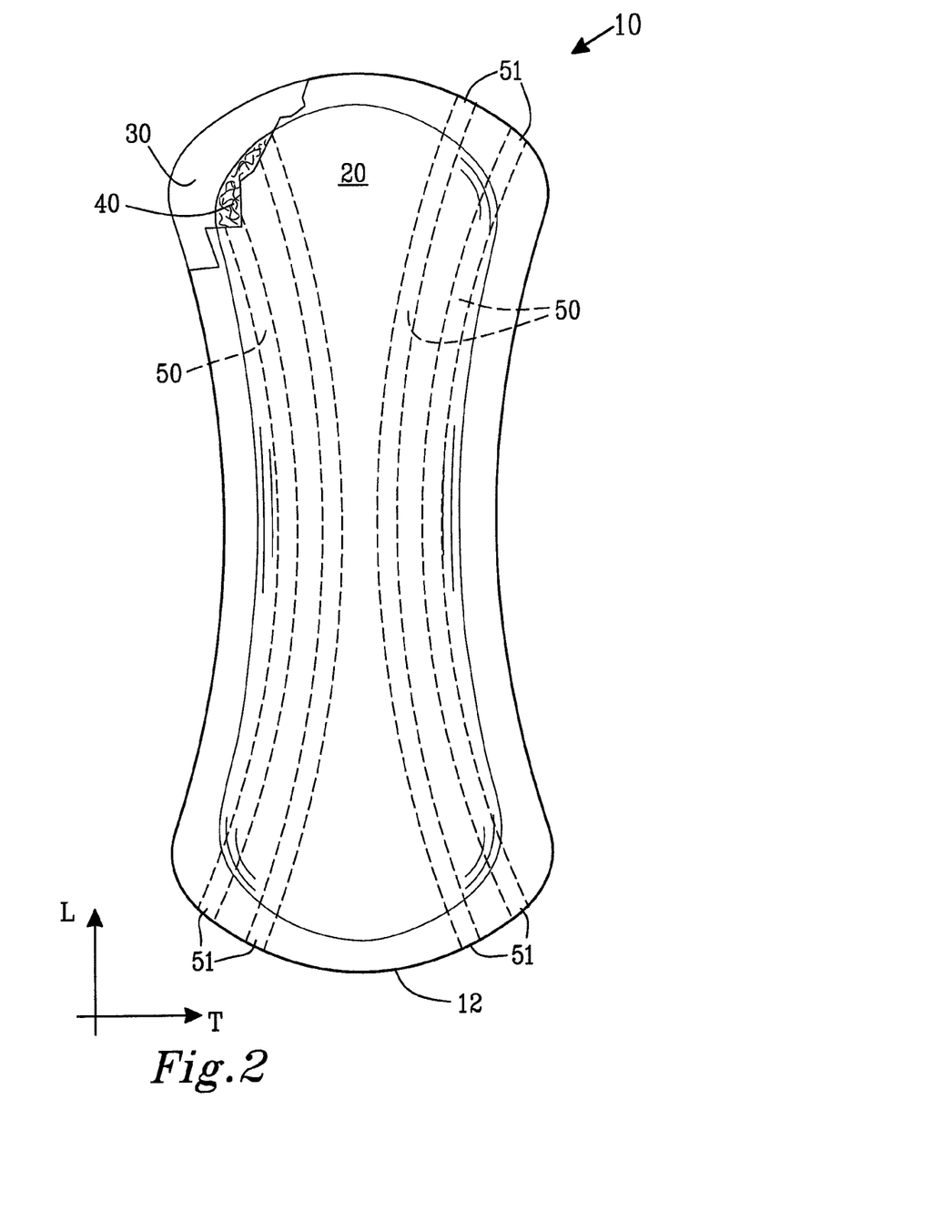
FIG. 2 illustrates an embodiment of the absorbent article.
Figure 3:
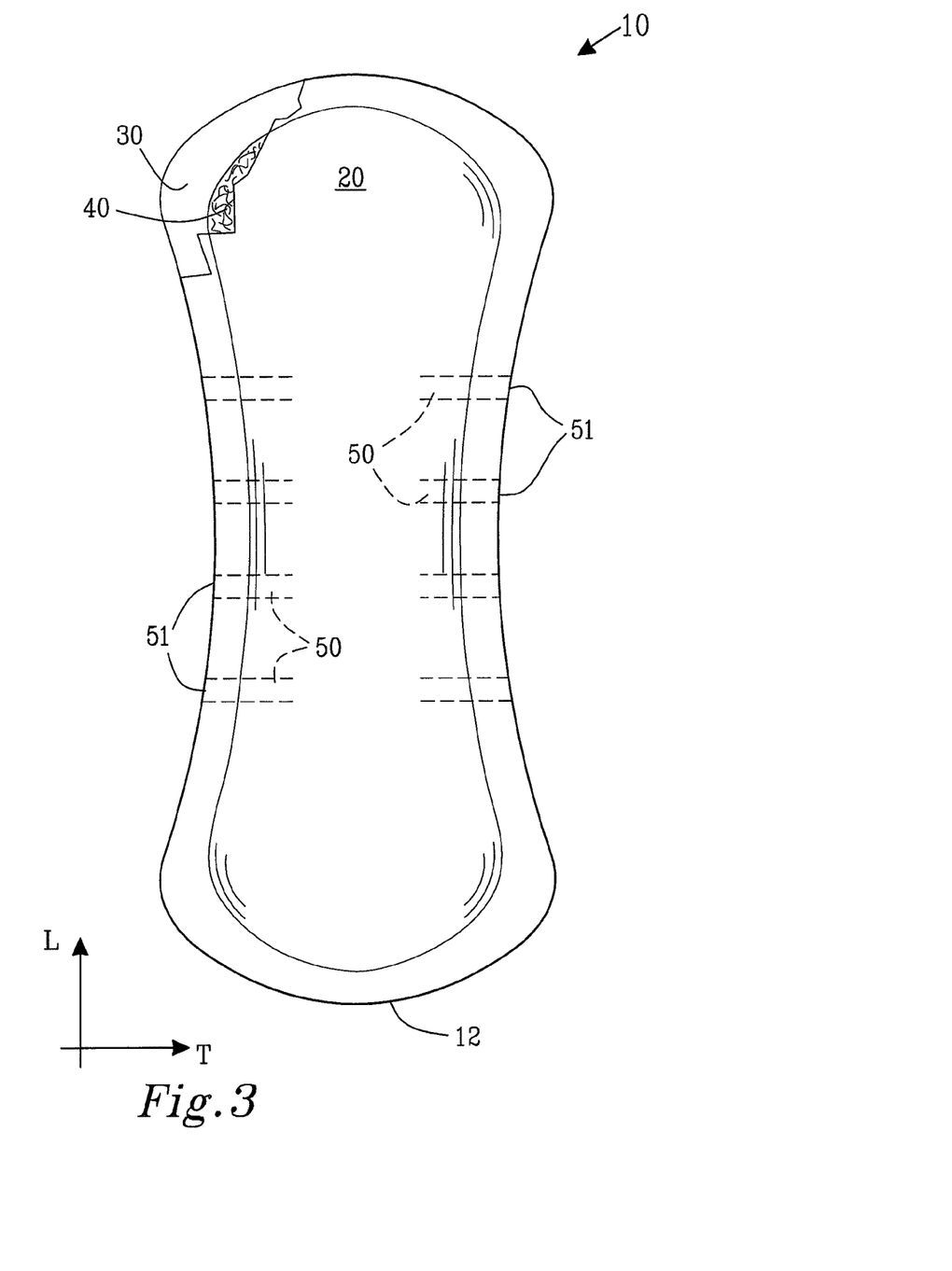
FIG. 3 illustrates an embodiment of the absorbent article.

The nonwoven topsheet 20 includes a plurality of channels 50 arranged side-by-side (FIGS. 1-3). By "side-by-side" is meant that longest edges of neighboring channels 50 substantially flank each other, as illustrated in FIGS. 1-3. The channels 50 are arranged side-by-side in the L-T plane of the article 10. In particular embodiments, the channels 50 are arranged side-by-side in the transverse direction T of the article 10 and have their main extension aligned in the longitudinal direction L of the article 10 (FIGS. 1 and 2). However, the channels 50 may also be arranged side-by-side in the longitudinal direction L of the article 10 and have their main extension aligned in the transverse direction T of the article 10 (FIG. 3). A "plurality of channels" means more than one channel, preferably more than 2 channels, more preferably more than 3 channels, such as for example 4, 5, 6, or 10 channels.

Figure 4:
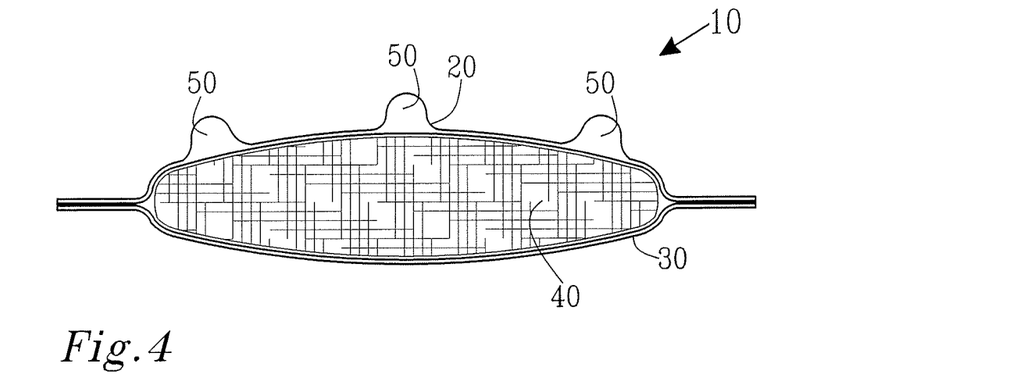
FIG. 4 is a cross-section through the line IV-IV in FIG. 1.

The channels 50 are located within the nonwoven topsheet 20. By "within" is meant that they are surrounded on all sides by the fibers of the nonwoven topsheet (see FIG. 4). Indeed, in particular embodiments, the walls of the channels 50 are defined by the fibers of the nonwoven topsheet. In more particular embodiments, the walls of the channels 50 are liquid-impermeable, so that the ventilating effect is not blocked by liquid, and the risk of liquid leaking from the article 10 via the channels 50 is reduced.

Depending on the relative dimensions of the channels 50 and the topsheet 20, spaces or voids may also be formed between the skin of the wearer and the topsheet 20, in the region of the topsheet 20 between adjacent channels 50, as the channel structure can hold the bulk of the topsheet 20 away from the wearer.

The channels 50 are regions within the nonwoven topsheet 20 which are substantially free from fibers 21. Gas may pass freely along the channels 50. The boundary between the channels 50 and the bulk of the nonwoven topsheet 20 may be gas-permeable, so that gas can pass freely into and out of the channels 50, for example via upper 22 or lower 24 layers. The channels 50 may also include openings or areas with lower fiber density. The walls of the channels 50 may also be sealed to gas, so that gas only passes into and out of the channels 50 via their ends. The channels 50 can have an elongated form, along which gas is free to pass. Although circular and oval cross-sections are illustrated in FIG. 5, the channels 50 may have any suitable cross-sectional shape.

The relative dimensions of the channels 50 within the topsheet 20 can be varied in order to provide optimal ventilation. For instance, adjacent channels 50 are separated (suitably in the transverse direction T, as per FIG. 1) by a distance T1, which depends on the nature of the article but may be as low as for example 5 mm for a small panty liner or sanitary napkin or as high as, for example, 300 mm for a large incontinence article for adults. The extension of the channels 50 in a given direction (for example the longitudinal direction L) of the article 10 may be at least 30%, preferably at least 50%, more preferably at least 70% of the extension of the article 10 in said direction. The channels 50 may even have an extension which is equal to the extension of the article in a given direction. In many embodiments, the length of the channels 50 lies between 2 cm and the entire extension of the article 10, preferably between 4 cm and the entire extension of the article 10. The width of the channels 50 can be between 2 and 10 mm, preferably between 3 and 5 mm.

At least one end 51 of the channels 50 extends to an edge of the article 10, for example the transverse edge 12, as shown in FIGS. 1 and 2, whereby gas is allowed to pass into, out of, and along the channels 50, thus providing ventilation of the absorbent article 10. The "transverse edge" is that edge which extends in the transverse direction. In this way, the channels 50 can lead gas from the center of the article to an edge. In a development of this embodiment, both ends of the channels 50 extend to an edge of the article 10, so that gas can enter or exit the channel 50 in the center of the article 10 and be transported to the edges. Gas may enter or exit the channels via the ends of the channels 50 or through the walls of the channels. In the embodiment of FIG. 1, the extension of the channels 50 in the longitudinal direction of the article 10 is the same as the extension of the article 10 in said direction; i.e. the channels extend from one edge of the article 10 to the other. Suitably, all channels 50 of the absorbent article 10 extend to an edge of the article 10, in particular the transverse edge 12.

Additionally, it may be that the channels 50 are open in at least one end 51 thereof and extend from an edge of the absorbent article 10 towards the middle of the absorbent article 10, as shown in FIG. 3. In particular embodiments, the channels 50 are not closed by adhesive, heat or ultrasonic sealing, by fibers 21, or by any other kind of material at either end. This arrangement is particularly effective as warm air/vapor present in the center of the absorbent article 10 (which generally lies between the wearer's legs) is free to escape from the absorbent article 10 via the open end 51 of channels 50.

The article 10 need not include the topsheet 20 over the entire article 10. It may be sufficient that the topsheet 20 is only located in regions of the article 10, such as for example the central region, the longitudinal end regions or the transverse end regions. Similarly, the channels 50 need not be located over the entire wearer-facing surface of the article 10 as shown in FIG. 1; it is conceivable that they are only located in regions of the article 10, such as for example the central region or the transverse or longitudinal end regions. Of particular interest is the situation in which channels 50 are located in the transverse end regions and extend in the longitudinal direction. In this way, the channels may also act as barriers to limit or prevent undesired liquid flow towards the transverse edges of the article 10, which is a common source of leakage.

The channels 50 need not be linear, as they are in FIG. 1. They may be curved or even meet. In this way, the channels 50 may form patterns in the topsheet 20, which can provide folding or wearing indications, or barriers as described above which can follow the curvature of an edge of the article 10.

FIG. 2 shows an absorbent article 10 which includes the above features. Channels 50 are located in the transverse edge regions and have their major extension in the longitudinal direction of the article 10. The channels 50 are also curved as shown, so that they follow the curvature of the longitudinal side edges. The combination of the location and form of the channels in FIG. 2 provides an effective barrier to liquid flow in the transverse direction of the article 10.

In a particular embodiment, the interiors of all channels 55 are substantially free of solid or liquid material. This ensures that passage of gas along the channels 50 is not obstructed.

Figure 5A:
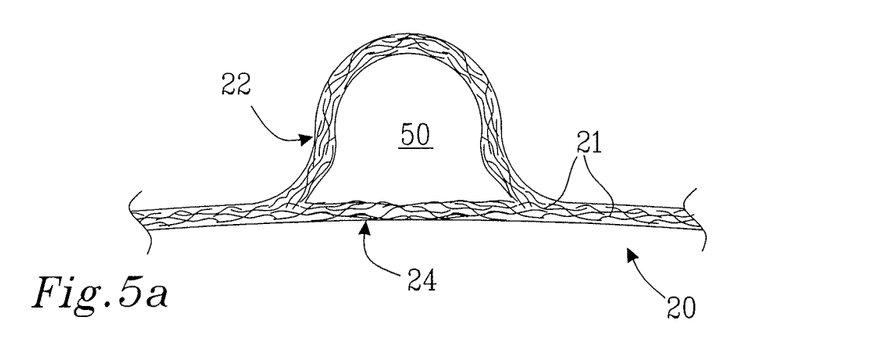
FIGS. 5a-5d are magnified embodiments of the topsheet.
Figure 5B:
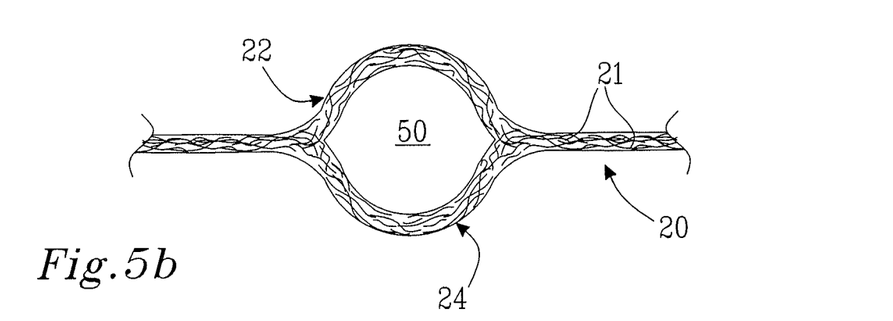
Figure 5C:
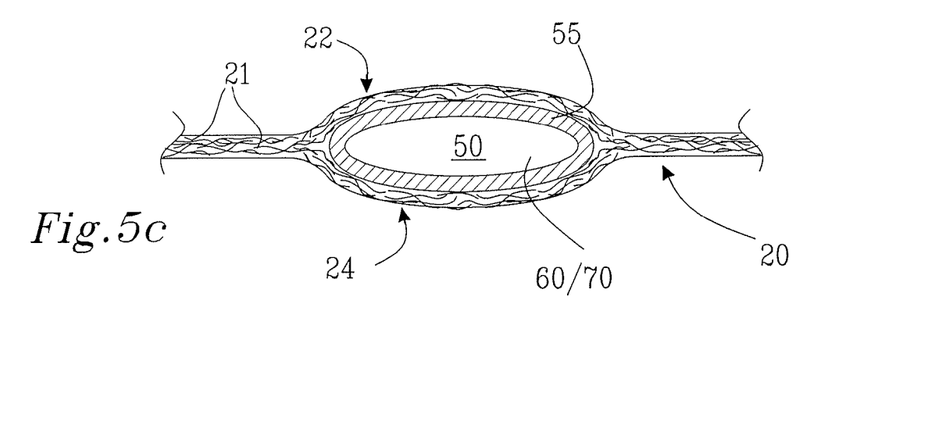
Figure 5D:
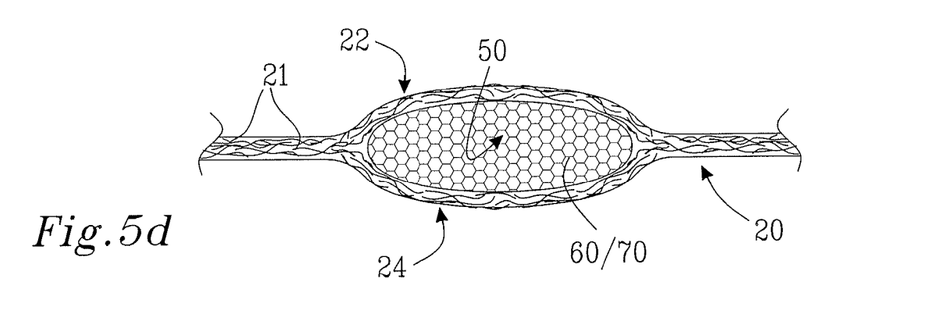

Alternatively, some (i.e. at least one but not all) of the channels 50 may contain moisture-capturing and/or liquid-absorbent material 60, which provides moisture-capturing capability or an extra reservoir for liquid absorption in the absorbent article 10 (see FIG. 5d). Suitable moisture-capturing materials 60 may be silica (in particulate or powder form), superabsorbent powder supported on a carrier (for example fibers) and zeolites. Absorbent materials 60 suitable for incorporation into the channels 50 include both natural and synthetic absorbent materials. Natural absorbent materials include cellulose fluff pulp. Synthetic absorbent materials include so-called superabsorbent polymers, such as the polymer of acrylic acid and the partly-neutralized polymer of acrylic acid. Other suitable absorbent materials 60 are those described as components of the absorbent core 40 below. It is important that, to maintain ventilation in the topsheet 20, only some of the channels 50 contain absorbent material 60, while others are empty. In particular embodiments, those channels 50 including absorbent material 60 are arranged towards the edges of the absorbent article 10, which provides extra protection against edge leakage.

As a further alternative, some (i.e. at least one but not all) of the channels 50 may contain phase change material 70 (see FIG. 5d), which is a material which exhibits a reversible phase-change upon uptake or release of heat energy. In this way, temperature fluctuations within the topsheet 20 can be evened out, which improves comfort. Examples of useful phase change materials are wax, paraffin and sodium sulfate decahydrate (Glauber's salt). It is important that, to maintain ventilation in the topsheet 20, only some of the channels 50 contain phase change material 70, while others are empty.

Some (i.e. at least one but not all) of the channels 50 may contain a skin-care agent. Suitable skin-care agents are described in EP 1 227 776 and WO 96/16682.

It is also advantageous if the inner surfaces of the channels 50 are treated to make them hydrophobic. In this way, liquid is discouraged from entering the channels 50 and blocking the passage of gas. Hydrophobic treatment provides a surface which has a contact angle with water of above 90 degrees as measured by TAPPI method T558PM-95 (1995). Hydrophobic treatment can be achieved by coating with for example fluoro-containing monomers, followed by polymerization. Treatment with silicone can also provide a hydrophobic surface.

In another embodiment, the channels 50 include hollow filaments 55 (FIG. 5c). The filaments 55 form the walls of the channels 50. These filaments 55 have a diameter which corresponds to the diameter of the channels 50, and are aligned to extend inside the channels 50. In this way, they lie within the topsheet 20 and support the structure of the channels 50. The walls of the filaments 55 may be gas-permeable, so that air and vapor can enter or leave the filaments 55. Alternatively, the walls of the filaments may be gas-impermeable, so that gas only enters or leaves the filaments via the ends.

The filaments 55 may also be open in at least one end thereof, as described above for channels 50. Some (i.e. at least one but not all) of the filaments 55 may contain absorbent material 60, phase change material 70 and/or skin care agent, as described above for channels 50.

The channels 50 may also comprise porous material, for example a foam material which provides a cushioning effect in the topsheet. The porous material should be open-celled, so that gas is not hindered from passing into and/or along the channel 50. A fibrous material may also provide resilient and lofty structures.

The topsheet 20 may have a certain minimum compression recovery, where, for example, after being compressed completely, it rapidly recovers its original thickness. This helps the channels 50 to maintain their open structure and recover their form when subjected to physical pressure, for example when the person wearing the absorbent article sits or lies down. As the open structure of the channels is maintained, passage of air through the channels is not hindered, and ventilation can easily occur. Suitably, the compression recovery of the topsheet 20 is at least 50%, preferably at least 70%, more preferably at least 80%, most preferably 100%. If the topsheet has a compression recovery of for example at least 70%, it means that the topsheet recovers at least 70% of its original thickness (caliper) upon removal of the compressive force. The thickness of the topsheet 20 may be measured by EDANA method WSP 120.6 (2005).

In the case where the channels 50 include hollow filaments 55, the topsheet 20 may also have the certain minimum compression recovery set out above. Again, this helps the channels 50 to regain their open structure when subjected to physical pressure, for example when the person wearing the absorbent article sits or lies down.

The absorbent article 10 illustrated in FIGS. 1-4 includes a liquid-impermeable backsheet 30. This backsheet 30 may include a thin plastic film, for example a polyethylene or polypropylene film, a nonwoven material coated with a liquid impervious material, a hydrophobic nonwoven material which resists liquid penetration, or a laminate of plastic films and nonwoven materials. The backsheet 30 may be breathable so as to allow vapor to escape from the absorbent core, while still preventing liquids from passing through the backsheet material. The backsheet 30 may be elastic.

Fasteners, like friction fasteners, tape tabs or mechanical fasteners like hook-and-loop fasteners etc. may be used to fasten the absorbent article 10 of the invention to the underwear or around the waist of the wearer. Some absorbent articles are in the form of pants and therefore do not need special fastening means. In other cases the absorbent article is worn in special elastic pants without the need for additional fasteners.

Similarly, elastic elements may be included in the absorbent article 10 to improve fit and reduce leakage. Exemplary elastic elements are waist elastics, leg elastics and so-called "standing gathers". Suitable elastic elements are known to the skilled person and need not be discussed further here.

The article illustrated in FIGS. 1-4 includes an absorbent core 40, which can be of any conventional kind. Examples of commonly occurring absorbent materials are cellulosic fluff pulp, tissue layers, airlaid cellulose material, highly absorbent polymers (so called superabsorbents), absorbent foam materials, absorbent nonwoven materials or the like. It is common to combine cellulosic fibers with superabsorbents in an absorbent core. It is also common to have absorbent cores including layers of different material with different properties with respect to liquid acquisition capacity, liquid distribution capacity and storage capacity. The thin absorbent cores often include a compressed mixed or layered structure of cellulosic fibers and superabsorbent material. The size and absorbent capacity of the absorbent core may be varied to suit different uses such as sanitary napkins, pantiliners, adult incontinence pads and diapers, baby diapers, pant diapers, etc.

The nonwoven topsheet can be manufactured using methods corresponding to the methods described in WO2005/007962. WO2005/007962 describes a method for producing a so called nonwoven spacer fabric.

A spacer device is used to separate two fibrous web layers and fine columnar high pressure jets are directed on to the fibers to bond and interconnect the separate fibrous layers on and between the elements of the spacer device. Two fibrous webs (corresponding to layers 22, 24) are positioned on either side of a spacer device. The spacer device may include uniformly spaced cylindrical members. While located on either side of the spacer device, the fibrous webs are then subjected to hydroentanglement, from one or both faces of the topsheet, so that fibers move from the individual webs into the regions between the spacer device. In this way, channels 50 are formed. Curved channels or channels that meet may be obtained by moving the elements of the spacer device relative to one another during the manufacturing process. Movement of the webs over the spacer device causes the spacer device elements to be withdrawn from the web to produce an integrated 3D fabric structure with channel-like voids or cells in the cross-section running in the machine direction, which are formed by groups of fiber which periodically join the upper and lower layers of the fabric. The topsheet can be manufactured using circular spacer elements having a diameter from 0.3 or 0.4 mm up to 10 mm, which provides channels 50 with a cross-sectional area from 0.1 mm$^2$ to 80 mm$^2$, preferably 0.5 to 20 mm$^2$.

The fine columnar high pressure jets are the basic technology of high pressure water jets used to produce spunlace or hydroentangled materials. Whilst in contact with the spacer device, the fibrous layers will be impacted by water jets to both entangle fibers in the individual layers and to migrate fibers in to the Z-direction to interconnect the adjacent layers between spacer bar elements. In this way, the microstructure of internal channel-like voids/pores in the fabric is influenced by the shape and morphology of the spacer device used, process conditions and fiber properties.

In particular embodiments, when producing ventilated topsheets, the channels produced when the spacers are withdrawn are either left empty (air filled), fed with hollow filaments or fed with a substance adhering to the internal walls. For example, a foam material may be used to fill the channels, which either creates a porous filling supporting the channel, or collapses, leaving only a wall of film-like polymeric material which supports the channel.

Figure 6:
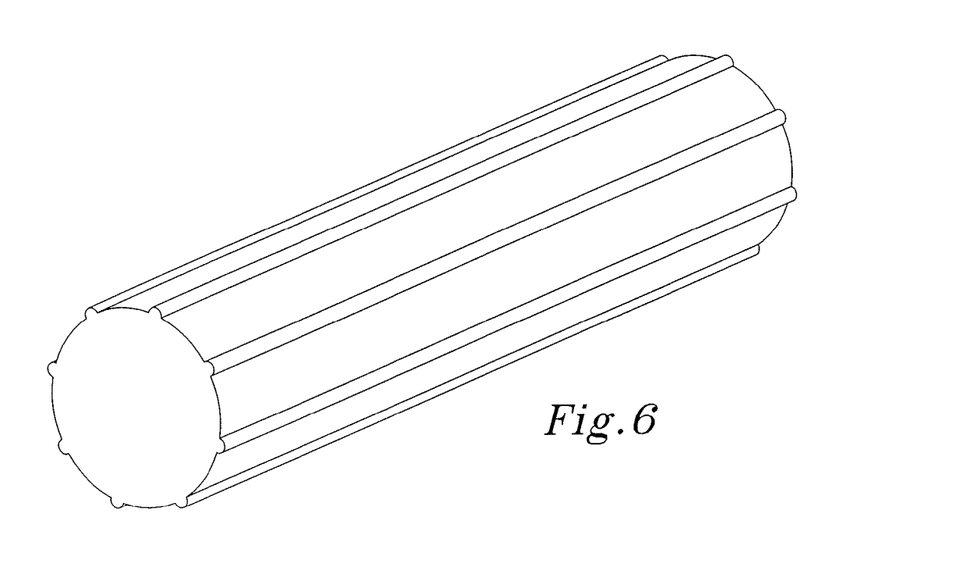
FIG. 6 shows a spacer device element used in the manufacture of the topsheet.

In a particular way of manufacturing the ventilated topsheets 20, the shape of the spacer device elements are cylindrical tubes with elevated longitudinal ridges, as shown in FIG. 6.

Upon the longitudinal elevated ridges, fibers will migrate away under the influence of the high pressure water jets, thus creating a web structure with a lower fiber density or openings along regions of the channels than in the closest surrounding area. The local low density of fibers or openings will allow for passage of gas in the ventilated topsheet from the volume between the product and the wearers skin, into the channels of the topsheet, or vice-versa (i.e. gas enters from outside).

In another way of manufacturing the ventilated topsheets, the water jet energy is concentrated at designated positions of the spacer device as compared to the average water jet energy across the material width, thus creating a web structure with a lower fiber density or openings along strands on the channels than in the closest surrounding area. Hence, a similar effect is seen from using the ridged spacer device of FIG. 6, yet with a smooth spacer device and simply by varying the water pressure. The local low density of fibers or openings can, in the ventilated topsheet, allow for passage of gas from the volume between the product and the wearers skin, into the channels of the topsheet or vice-versa.

In yet another way of manufacturing the ventilated topsheets, the water jet energy is concentrated at designated positions between the elements of the spacer device as compared to the average water jet energy across the material width, thus creating a web structure with a lower fiber density or openings in regions between the channels than in the closest surrounding area. This is especially effective if, while being subject to water jets, the topsheet is supported on a wire with raised elements located between the elements of the spacer device. In this way, fibers migrate away from the raised elements and simpler, larger holes can be obtained. The local low density of fibers can, in the ventilated topsheet, allow for passage of liquid through the topsheet into the absorbent product.

If the fibrous webs are hydroentangled primarily from one face, a material such as that shown in FIG. 5a is obtained, in which one fibrous web is deformed more than the other. If they are hydroentangled to a similar extent, both fibrous webs will be deformed, and a material such as that of FIG. 5b is obtained. FIG. 5c shows an embodiment which includes channels 50 with an oval cross-section. This embodiment allows similar air flow (as the cross-sectional area of the channel is the same as the circular embodiments of FIGS. 5a and 5b), yet has a thinner caliper. The embodiment of FIG. 5d incorporates moisture-capturing and/or liquid-absorbent material 60, phase change material 70 or skin care agent.

The method described above should be seen as a non-limiting example of methods that could be used for producing the ventilated topsheet. Other methods can also be used, for instance, by inserting a solid material or spacer element between two nonwoven layers and laminating them together by for example strings of adhesive, by ultrasonic welding, needling etc.

In the case where the channels 50 include hollow filaments 55, the topsheet 20 can be formed by laying hollow filaments 55 on a first nonwoven layer, overlaying a second nonwoven layer and hydroentangling the resulting laminate. The hollow filaments 55 remain within the topsheet 20.

Channels 50 containing solid material can be formed by laying rows of the solid material on a first nonwoven layer, overlaying a second nonwoven layer and hydroentangling the resulting laminate.

Embodiments of the invention have been described with reference to the embodied Figures. However, the invention is not limited to the above-described embodiments alone. For example, although the described embodiments related to particular reference to a sanitary napkin, it is equally applicable to other types of absorbent articles, for example diapers, incontinence guards or panty liners. Features from one or more of the above embodiments may be combined as required, and the ultimate scope of the invention should be understood as being defined in the appended claims.

The invention claimed is:

1. An absorbent article, said article comprising:
a fluid-permeable nonwoven topsheet located on the wearer-facing side thereof, said nonwoven topsheet comprising a plurality of channels arranged side-by-side, at a location of each channel the non-woven topsheet is separated into an upper layer and a lower layer with a corresponding channel formed therebetween,
wherein at least one end of at least one channel extends in a direction to the furthest extent of the article in said direction, and
wherein the plurality of channels are configured to provide ventilation of the absorbent article by allowing gas to pass in and out of the plurality of channels.

2. The absorbent article according to claim 1, wherein the article has longitudinal and transverse extensions, and wherein the channels are arranged side-by-side in the transverse direction of the article and have a main extension in the longitudinal direction of the article.

3. The absorbent article according to claim 2, wherein the extension of the channels in the longitudinal direction is at least 30% of the extension of the article in the longitudinal direction.

4. The absorbent article according to claim 2, wherein the extension of the channels in the longitudinal direction is at least 50% of the extension of the article in the longitudinal direction.

5. The absorbent article according to claim 2, wherein the extension of the channels in the longitudinal direction is at least 70% of the extension of the article in the longitudinal direction.

6. The absorbent article according to claim 1, wherein the article has longitudinal and transverse extensions, and wherein the channels are arranged side-by-side in the longitudinal direction of the article and have a main extension in the transverse direction of the article.

7. The absorbent article according to claim 6, wherein the extension of the channels in the transverse direction is at least 30% of the extension of the article in the transverse direction.

8. The absorbent article according to claim 6, wherein the extension of the channels in the transverse direction is at least 50% of the extension of the article in the transverse direction.

9. The absorbent article according to claim 6, wherein the extension of the channels in the transverse direction is at least 50% of the extension of the article in the transverse direction.

10. The absorbent article according to claim 1, wherein spaces or voids are formed between skin of the wearer and the topsheet in the region of the topsheet between adjacent channels.

11. The absorbent article according to claim 1, wherein the channels are substantially free of solid or liquid material.

12. The absorbent article according to claim 1, wherein at least one but not all of the channels contains moisture-capturing, liquid-absorbent material, phase change material, skin care agent, or any combination thereof.

13. The absorbent article according to claim 1, wherein the channels are open in at least one end thereof.

14. The absorbent article according to claim 1, wherein at least one channel of the absorbent article extends to the transverse edge of the article.

15. The absorbent article according to claim 1, wherein the channels comprise hollow filaments, said filaments forming the walls of the channels.

16. The absorbent article according to claim 1, wherein the channels comprise porous material or resilient fibrous material.

17. The absorbent article according to claim 1, wherein the compression recovery of the topsheet is at least 50%.

18. The absorbent article according to claim 1, wherein the compression recovery of the topsheet is at least 70%.

19. The absorbent article according to claim 1, wherein the compression recovery of the topsheet is at least 80%.

20. The absorbent article according to claim 1, wherein the compression recovery of the topsheet is at least 100%.

21. The absorbent article according to claim 1, wherein the upper layer and the lower layer of the non-woven topsheet are substantially free from fibers.

22. The absorbent article according to claim 1, wherein side edges of the absorbent article are curved, and the plurality of channels are curved to follow a curvature of the side edges.

* * * * *